United States Patent
DeCorso et al.

(12)

(10) Patent No.: US 6,230,103 B1
(45) Date of Patent: May 8, 2001

(54) METHOD OF DETERMINING CONCENTRATION OF EXHAUST COMPONENTS IN A GAS TURBINE ENGINE

(75) Inventors: Mario DeCorso, Media, PA (US); Alexandr A. Belokon, Moscow (RU); Yuri Ya. Buriko, Moscow (RU); Vladimir M. Zakharov, Moscow (RU); Paul C. Holden, Newtown Square; David L. Moen, Glen Mills, both of PA (US)

(73) Assignee: Power Tech Associates, Inc., Media, PA (US)

( * ) Notice: Subject to any disclaimer, the term of this patent is extended or adjusted under 35 U.S.C. 154(b) by 0 days.

(21) Appl. No.: 09/195,937

(22) Filed: Nov. 18, 1998

(51) Int. Cl.[7] .................................................. G01N 31/00

(52) U.S. Cl. .............................. 702/23; 702/24; 73/23.31; 60/39.27

(58) Field of Search .......................... 702/22–26, 29–36, 702/104, 113, 114, 127, 128, 182–185, 45, 50, 100; 73/23, 31; 60/39.27, 39.03, 274, 277, 39.2; 700/271, 273, 266

(56) References Cited

U.S. PATENT DOCUMENTS 5,024,055  *  6/1991  Sato et al. ............................ 60/39.27
5,257,496  *  11/1993  Brown et al. ........................ 60/39.06

* cited by examiner

*Primary Examiner*—Marc S. Hoff
*Assistant Examiner*—Manuel L. Barbee
(74) *Attorney, Agent, or Firm*—William H. Eilberg

(57) ABSTRACT

A method of determining the concentration of an exhaust component in a gas turbine engine includes measuring the concentration of the selected component at a single location, and using the measured concentration in a simple equation which yields a calculation of concentration in the engine exhaust. Use of this method requires that a measurement be taken for only one of multiple combustors in an engine, but the result is valid for the entire engine. Thus, the method can reduce the cost of design and development of new combustors for gas turbine engines, since it does not require that multiple combustors be built before the engine is tested. The sampling of the component of interest is done at a point sufficiently downstream that the concentration of the component has become relatively stable. The invention also includes an engine having one or more combustors modified to include a probe, and its associate analyzer, at an optimum location. The analyzer may be connected to a computer which is connected to a display device, to provide continuous monitoring of the emissions performance of the ensemble of combustors.

37 Claims, 5 Drawing Sheets

TRANSVERSE AND LONGITUDINAL PROFILES OF SPECIES
CONCENTRATION IN TURBULENT JET DIFFUSION FLAME

TRANSVERSE AND LONGITUDINAL PROFILES OF SPECIES
CONCENTRATION IN TURBULENT JET DIFFUSION FLAME

SPECIES CONCENTRATION MEASUREMENTS AT THE EXIT OF COMBUSTOR

SPECIES CONCENTRATION MEASUREMENTS AT THE EXIT OF COMBUSTOR

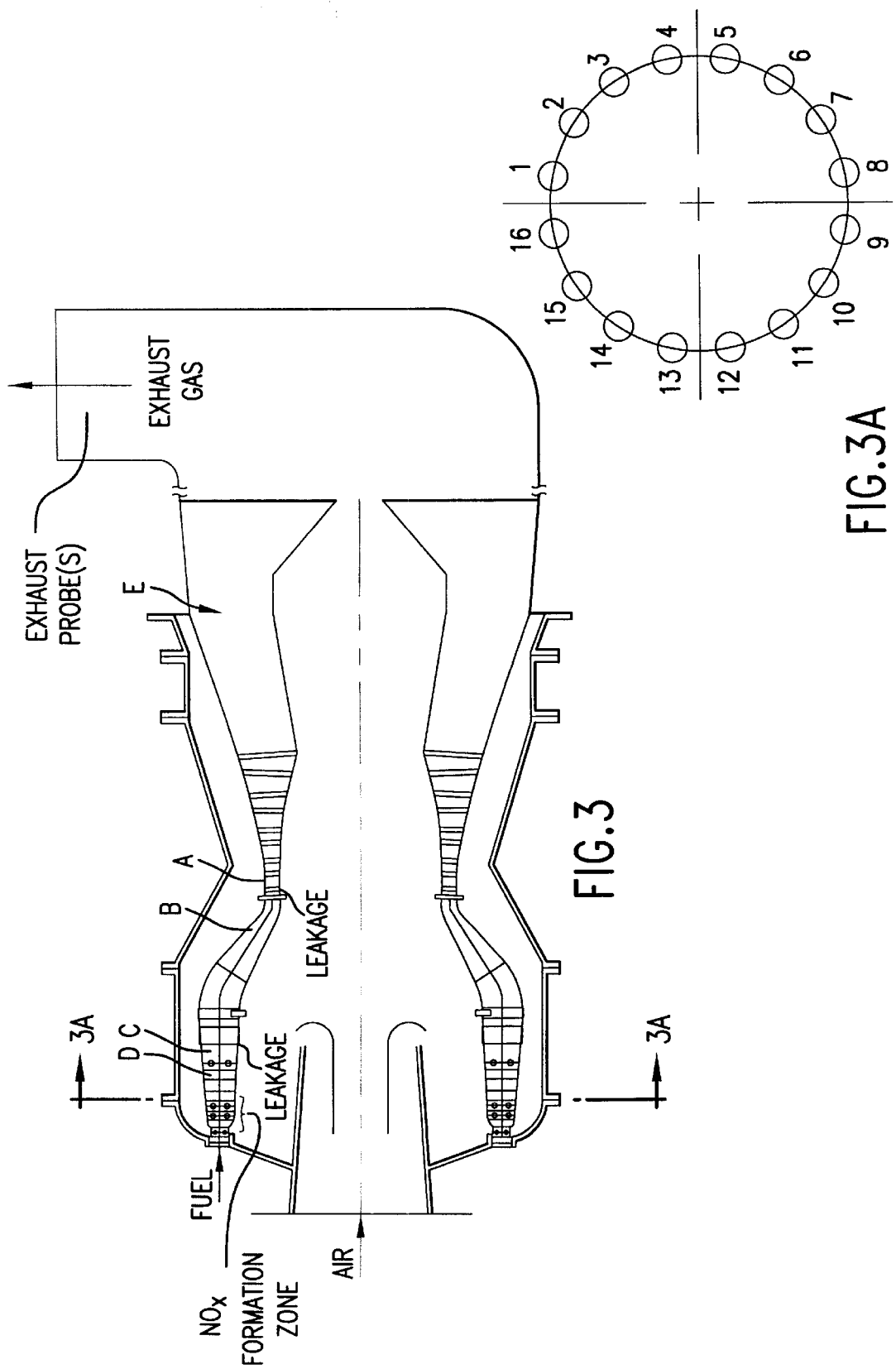

METHOD OF DETERMINING CONCENTRATION OF EXHAUST COMPONENTS IN A GAS TURBINE ENGINE

BACKGROUND OF THE INVENTION

This invention relates to gas turbine engines, such as those used in aircraft or in utility power plants. The invention provides an economical method of determining the concentration of a component of the exhaust gas of the engine, based on measurements taken at a single point probe, located well upstream of the exhaust stack, such as in one combustor of the engine.

A gas turbine engine, such as that used in an aircraft or a utility power plant, includes a compressor, a combustion section, and a turbine. Typically, the combustion section includes a plurality of separate combustors, arranged in a circle around a central axis so that the combustors act in parallel. The combustors are sometimes called "cans", and the arrangement is referred to as can-annular.

In the design of turbine engines, an important criterion is the level of emissions of various combustion products, especially NOx and carbon monoxide (CO). When the structure of a combustor is proposed to be modified, it is necessary to know how much NOx and/or CO will be emitted by an engine built with combustors having the modified design.

While some properties of the modified combustor, such as its temperature, can be measured directly, measurement of emissions presents a problem. A gas turbine engine typically has many combustors, sometimes as many as eighteen or twenty. A change in only one combustor will have a very small effect on the emissions of the entire engine, and this change is not usually large enough to measure accurately when masked by the contributions of all the others. Thus, in the prior art, in order to determine the concentration of NOx and/or CO in the exhaust of a modified engine, it was considered necessary to build a prototype of the complete engine, including all of its combustors, and to take actual measurements of exhaust products at a location where the exhaust gases are considered well mixed and completely uniform. This procedure is time-consuming and expensive, because it requires that one build and install a full complement of duplicate copies of a redesigned combustor, without knowing beforehand how well the combustor will work.

The present invention solves the above-described problem, by providing a method of determining the concentration of an exhaust component of an engine, which method requires measurements to be taken at only one of the combustors of the engine. Therefore, the present invention eliminates the need to build multiple prototypes when developing a new combustor. The invention also provides a diagnostic method and apparatus for monitoring the performance of an engine, and for taking action when the performance of one of its combustors deteriorates.

SUMMARY OF THE INVENTION

In one embodiment, the method of the present invention begins with the step of providing a modified combustor for inclusion in a gas turbine engine having multiple combustors. One then operates the modified combustor, while measuring the concentration of an exhaust component of interest (such as NOx or CO), at a single and specified point in the modified combustor, and while also measuring the concentration of carbon dioxide ($CO_2$), at the same point in the same combustor. The concentration of $CO_2$ in the exhaust of the entire engine is calculated from known principles, from a knowledge of engine air flow, fuel flow, and the hydrogen/carbon ratio in the fuel. Alternatively, the $CO_2$ concentration in the exhaust can be measured directly. From the foregoing quantities, one computes the concentration of the component of interest in the exhaust of the entire engine. The calculation can be expressed as:

$$X_{exhaust} = (X_{sample}/CO2_{sample}) \times CO2_{exhaust}$$

where $X_{exhaust}$ is the concentration, in the entire engine exhaust, of the component of interest;

$X_{sample}$ is the measured concentration, at one point in the modified combustor, of the component of interest;

$CO2_{sample}$ is the measured concentration of $CO_2$, at one point in the modified combustor; and $CO2_{exhaust}$ is the calculated or measured concentration of $CO_2$ at the exhaust outlet of the entire engine.

In a more general form, the method does not require redesign of a combustor, but can simply be used to determine the concentration of an exhaust component based on measurements taken at a single existing combustor. The invention can also be used to compare the performance of the various combustors in an engine. In another embodiment, the invention can be used to monitor the performance of the combustors of an engine, by making continuous calculations of concentrations of exhaust components, and by providing a visual or aural indication when an anomaly is detected.

The above-described method of determining concentration of exhaust components has been found to work well where the component of interest is NOx, but it can also be used to determine the emissions of CO and other components.

The invention also includes apparatus for performing the methods described above.

The present invention therefore has the primary object of providing a method of determining emissions of a gas turbine engine.

The invention has the further object of providing a method as described above, wherein measurements need be taken only at a single point in a single combustor.

The invention has the further object of simplifying the process of testing a newly-designed combustor.

The invention has the further object of substantially reducing the cost of testing a newly-designed combustor.

The invention has the further object of providing information which leads to the design of engines having reduced emissions of pollutants, with minimal cost.

The invention has the further object of providing method and apparatus for monitoring the performance of a gas turbine engine.

The invention has the further object of providing apparatus and methods for indicating an anomaly in emissions of a gas turbine engine.

The reader skilled in the art will recognize other objects and advantages of the present invention, from a reading of the following brief description of the drawings, the detailed description of the invention, and the appended claims.

BRIEF DESCRIPTION OF THE DRAWINGS

FIG. 3 provides a longitudinal cross-sectional view of an engine used in the practice of the method of the present invention.

FIG. 3a provides a cross-sectional view taken along the line 3a—3a of FIG. 3, showing the arrangement of combustors disposed around the longitudinal axis of the engine.

DETAILED DESCRIPTION OF THE INVENTION

The method of the present invention makes it possible to determine the emissions of a gas turbine engine, by taking measurements only at a single point at one of the combustors of the engine. With this method, one can modify the structure of only one of the combustors of an engine, and determine the emissions of an engine in which all of the combustors are so modified. Thus, the invention greatly reduces the time and cost required to perform a test program.

The invention is not limited to use in developmental programs. Variations of the same method can be used to monitor the performance of an engine, such as by continuously comparing the performance of the combustors of an engine, and/or by providing an indication when the performance of a combustor deteriorates.

Figure 1A:
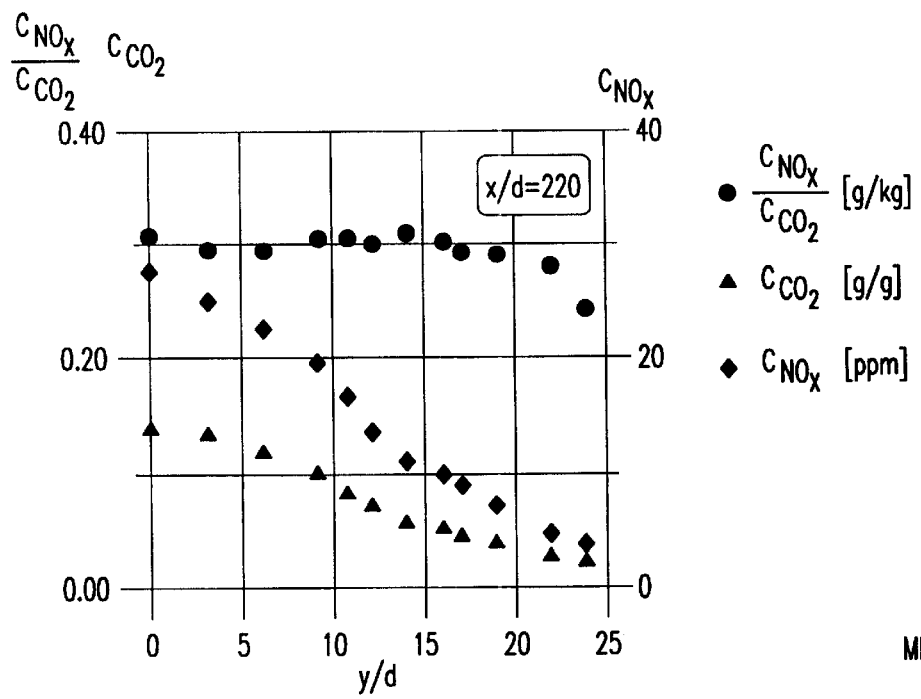
FIGS. 1a and 1b provide graphs showing transverse and longitudinal profiles of concentration of components measured in a combustion flame, these graphs showing the theoretical underpinning for the operation of the present invention, and FIG. 1c provides a diagram defining the variables plotted in the graphs.
Figure 1C:
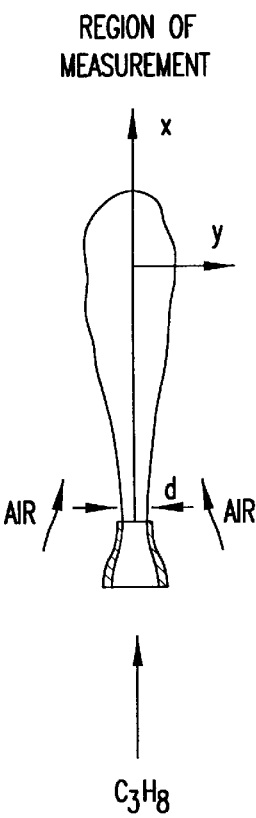
Figure 1B:
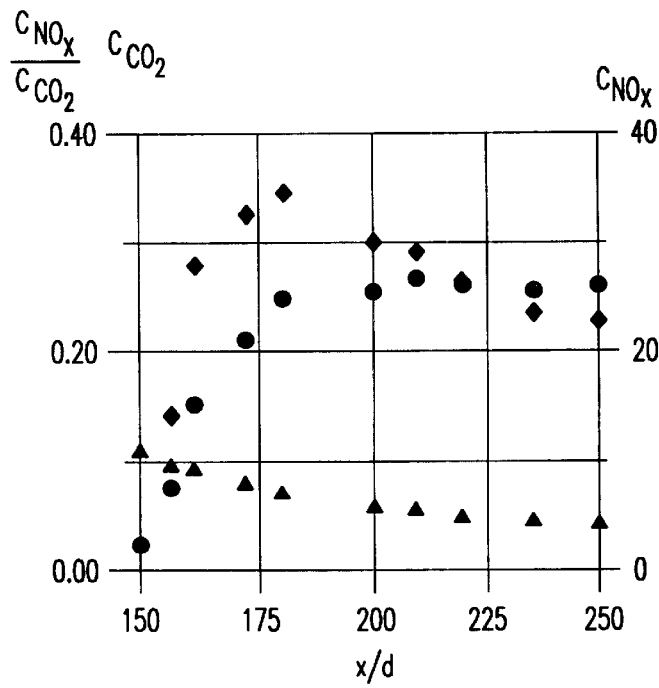

The theory underlying the method of the present invention is illustrated by the graphs of FIGS. 1a and 1b, and 2a and 2b. FIGS. 1c and 2c indicate diagrammatically the physical arrangements associated with their respective graphs. FIGS. 1a and 1b show the concentrations of $CO_2$ and NOx in a flame, as well as the ratio of the concentration of NOx to that of $CO_2$, at various transverse (FIG. 1a) and longitudinal (FIG. 1b) positions, in various laboratory tests. As shown in FIG. 1a, the ratio of concentration of NOx to concentration of $CO_2$ (represented by the solid circles) is relatively constant across the flame, and drops only at the outer boundaries of the flame zone. As shown in FIG. 1b, the same ratio becomes relatively constant with longitudinal distance, after an initial increase.

Figure 2A:
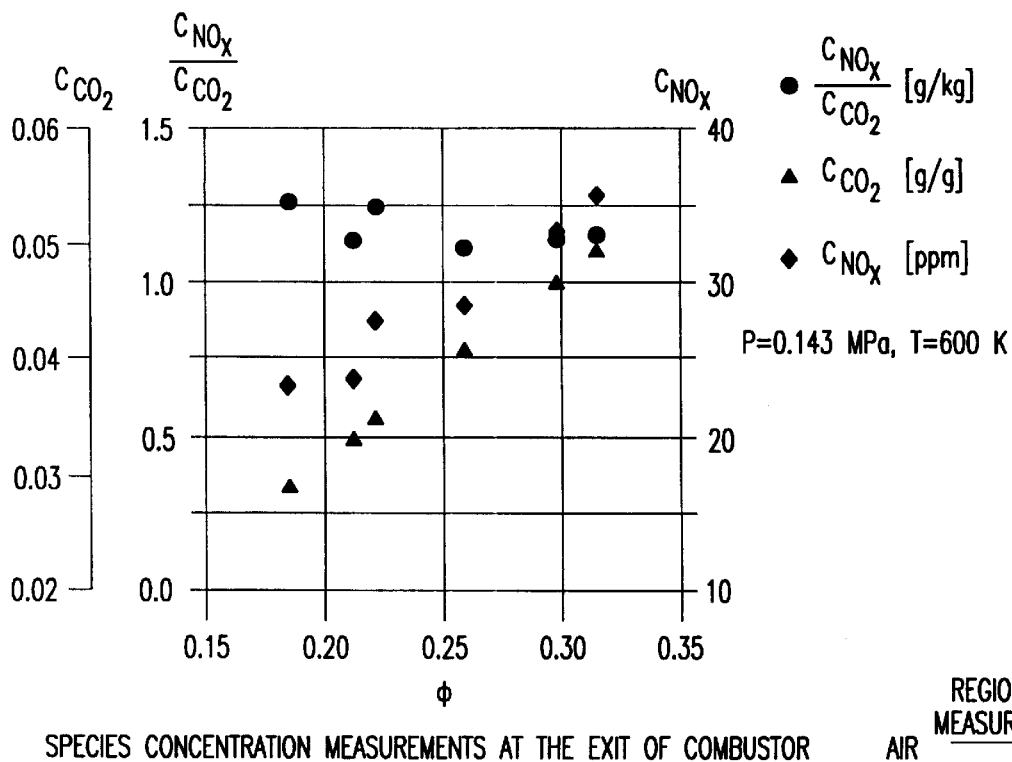
FIGS. 2a and 2b provide graphs showing concentration of components measured near the exit end of a combustor, such as that used in the present invention, and FIG. 2c provides a diagram showing the physical arrangement used in creating the graphs.
Figure 2C:
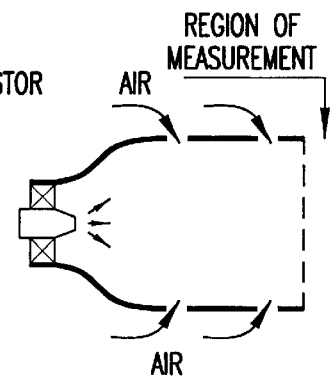
Figure 2B:
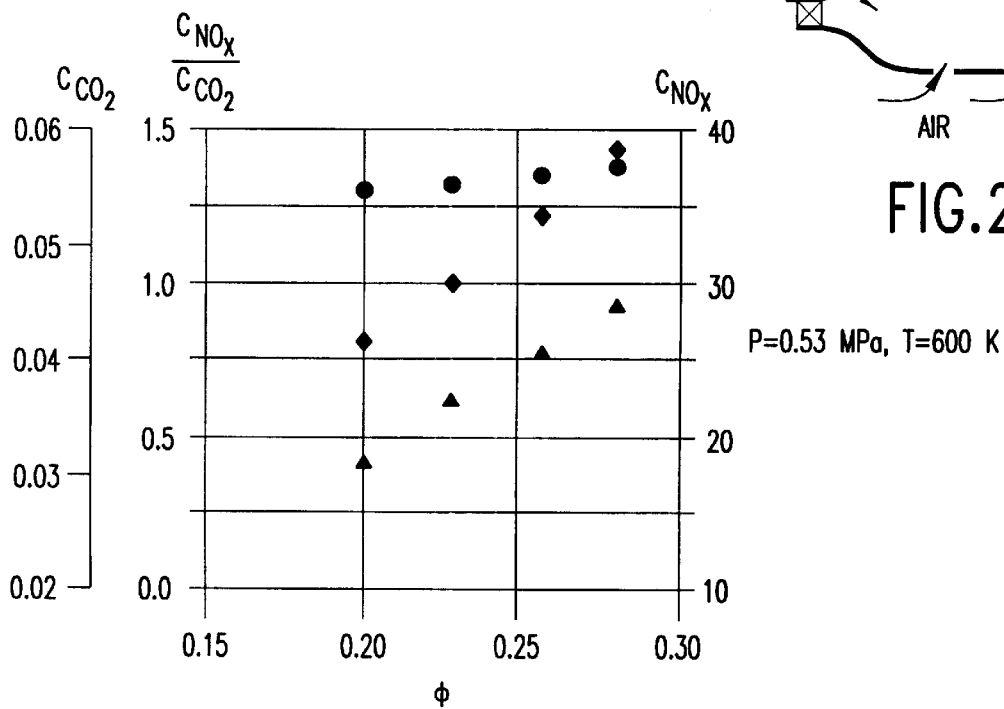

The same conclusion is apparent from FIGS. 2a and 2b, which show the same concentration ratios, taken near the exit end of a combustor, plotted against the equivalence ratio, which is a ratio of fuel to air. When air is present in an amount exactly equal to the stoichiometric requirement for complete combustion of the fuel, the equivalence ratio is one. In FIGS. 2a and 2b, the solid circles trace a generally horizontal line, implying that the ratio of concentrations remains approximately the same for various values of the equivalence ratio.

FIGS. 1 and 2 therefore imply that the path of NOx and $CO_2$ through a flame front is essentially the same, and that, once quenched to a still reasonably high temperature, the compounds travel together through subsequent mixing processes without further appreciable formation of combustion products or burnout. The additional $CO_2$ formed by burnout of CO is negligible compared to the total amount of $CO_2$.

In the case of NOx, if the mixing process caused by the introduction of secondary air into the combustion zone of the combustor is relatively complete, the ratio of concentration of NOx to $CO_2$ in the mixture, in or near the diluent zone of the combustor, will be unchanged by further mixing with diluent air, leakage air, or turbine cooling air. Thus, a NOx and $CO_2$ measurement taken ahead of the point of introduction of diluent air (point D in FIG. 3), together with knowledge of the engine air and fuel flow, and the hydrogen to carbon ratio in the fuel, provides the information necessary to calculate the concentration of NOx in the exhaust of the engine.

The calculation is as follows:

$$X_{exhaust} = (X_{sample}/CO2_{sample}) \times CO2_{exhaust}$$

where $X_{exhaust}$ is the concentration, in the entire engine exhaust, of the component of interest;

$X_{sample}$ is the measured concentration, at one point in the modified combustor, of the component of interest;

$CO2_{sample}$ is the measured concentration of $CO_2$, at one point in the modified combustor; and $CO2_{exhaust}$ is the calculated or measured concentration of $CO_2$ at the exhaust outlet of the entire engine.

The above-described calculation yields the concentration of the component of interest, in the entire engine exhaust, in the case where all of the combustors are the same as the combustor in which the measurements are taken, and where the fuel flow to each combustor is the same.

The calculation of $CO2_{exhaust}$ is made according to basic physical principles, which will be known to those of ordinary skill in the art. Alternatively, one can measure this quantity directly. Thus, the present invention requires measurements to be taken at, at most, two different points. If $CO2_{exhaust}$ is calculated from basic principles, then the invention requires measurement at only a single point.

The measurements of concentration of the component of interest, and of $CO_2$, are taken at a single point in the combustor. The location of this single point should be chosen to be at or downstream of the point at which combustion is essentially complete, further NOx formation has ceased, and combustion gases are well mixed. Otherwise, the choice of location for sampling is dictated by considerations of mechanical convenience. If the sampling is done at a point at which combustion is complete, the ratio of concentrations obtained from the sampling (and appearing in the above equation) will remain relatively constant, even as the temperature changes in later stages of the engine.

FIG. 3 illustrates an engine, in cross-section, showing the paths for injection of fuel and combustion air, and showing various positions at which sampling may occur. FIG. 3a further illustrates the positions of the combustors; in the embodiment shown, there are 16 combustors, which are numbered in FIG. 3a. The positions at which sampling may occur are designated A, B, C, and D, in FIG. 3. In general, it is preferable to do the sampling further downstream, i.e. to the right in FIG. 3, to maximize the probability that the combustion gases are thoroughly mixed before the sampling is performed. On the other hand, it may be physically difficult to provide a probe at point A, due to the presence of the multiple vanes of the turbine. Point D may be easiest to insert a probe. Note that, at point D, not all of the combustor air has entered the combustion gas stream; diluent air and leakage air enter the stream later, as will be explained below.

Figure 4:
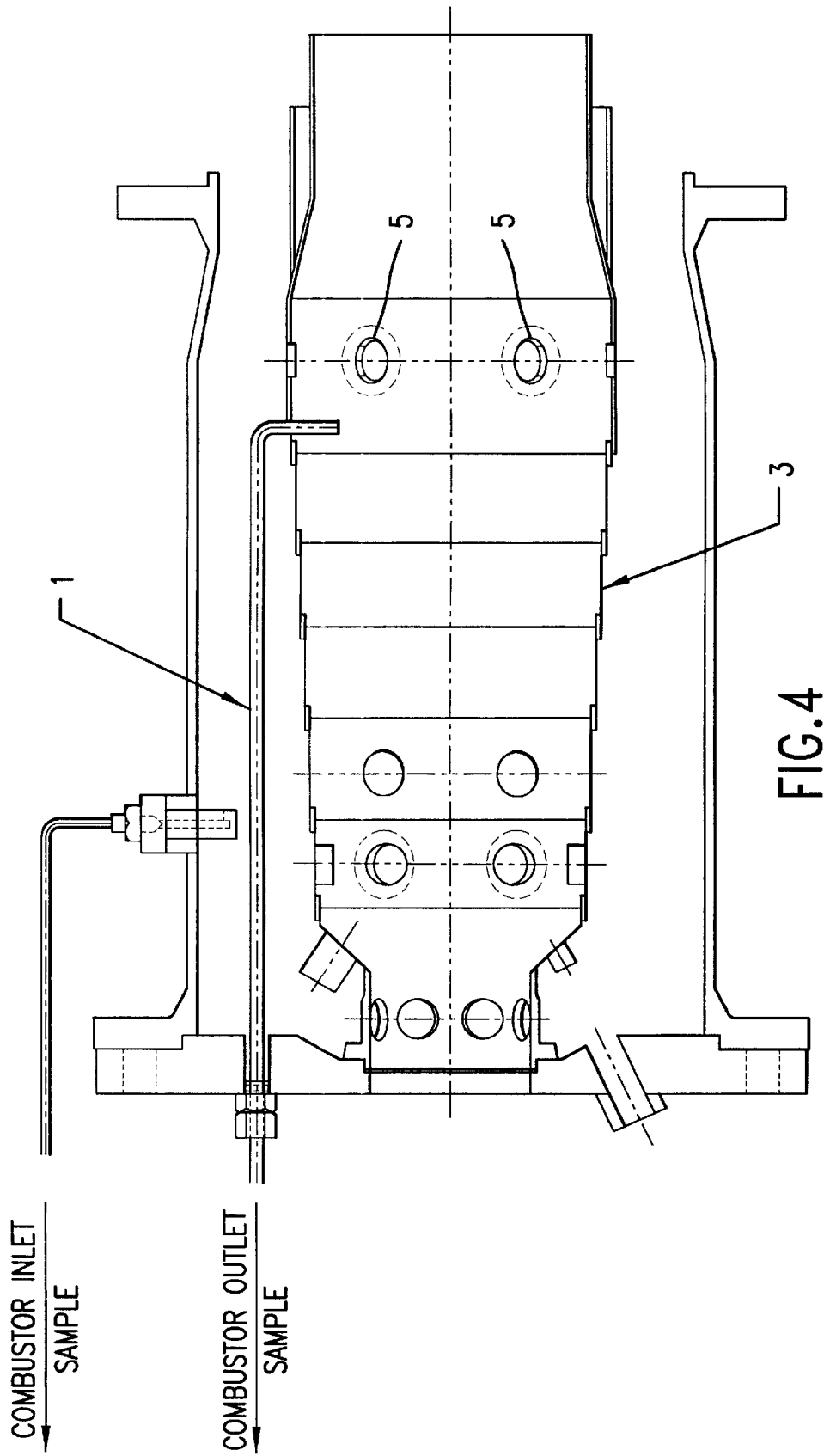
FIG. 4 provides a lateral cross-section of one of the combustors used in the engine of FIG. 3.

In the prior art, it was believed that, to evaluate the emissions performance of a turbine engine, one would need multiple samples throughout an entire cross-section of the combustor. The evaluation process was considered to require a very complicated sampling probe or sampling rake, to provide data from an elaborate array of sampling points at the end of a long, straight section of the exhaust duct. Often, such points would be quite high relative to ground level; exhaust stacks can often be forty feet high. With the method of the present invention, only a single, simple sampling probe is required. Such a probe is illustrated in FIG. 4. Moreover, the sampling probe of the present invention will be located at or near ground level, as is indicated by the points A through D in FIG. 3. In other words, the sampling can be done relatively close to the path of gas through the combustor, and not substantially higher than such path.

In the case where $CO2_{exhaust}$ is measured directly, this measurement may be taken at point E in FIG. 3. Point E lies substantially downstream of all of the combustors, so that the gases will normally be well mixed at this point. Point E, however, is still relatively close to the ground. Thus, by sampling the $CO_2$ in the exhaust of the entire engine at point E, one avoids the need to place a probe at the top of a very high exhaust stack.

The probe 1 of FIG. 4 is simply a heavy-walled tube which protrudes into combustor 3 at a position which corresponds to point D of FIG. 3. The end of the probe is located sufficiently far downstream that it is not in the hottest region of the combustor.

It is possible to position the probe further downstream, at point C of FIG. 3. Doing so would allow the sampling process to take into account the effect of diluent air, which lowers the temperature of the combustion gas so that the turbine blades can tolerate it. The diluent air enters through holes 5 of FIG. 4; these holes are also visible in FIG. 3. It may be physically somewhat more difficult to install a probe at point C.

Points A and B are considerably further downstream from points C and D. Point B is located in the transition area between the combustor and the turbine. It may be necessary to use point B for sampling CO, because the reactions involving CO are likely to continue longer than those for NOx.

The method of the present invention was tested with respect to NOx, in a gas turbine engine used in a utility plant. The engine used in the test had eight combustors. Combustor inlet and outlet samples were taken from the test combustor, which in this example was combustor No. 8, which had the general structure shown in FIG. 4. The sampling was done as indicated in FIG. 4. Thus, the combustor output was sampled at point D of FIG. 3. The results of the test are shown in Table 1.

Table 1 shows measurements for various levels of engine power, in megawatts. The concentration of NOx was measured, in each case, in parts per million by volume, dry, i.e. with compensation for the effect of water vapor in the sample. The table shows NOx concentrations as measured at the engine exhaust, and as calculated using the method of the present invention, from sample data taken from combustor No. 8 only. The last column of the table shows the ratio of measured engine exhaust to the engine exhaust calculated by the method of the present invention. All of these values are close to one, indicating that the method of the present invention worked extremely well, over a wide range of operating power.

Since NOx is formed only in the high-temperature portions of the combustor, the NOx reaction is essentially complete at the point where diluent air has been introduced through holes 5. The same is not true for carbon monoxide (CO). The CO to $CO_2$ reaction is still taking place in the region upstream of the introduction of diluent air, i.e. upstream of point C. Tests have confirmed that the method of the present invention does not work if the sampling of CO is performed at point D. However, the method is believed to be valid for CO if the sampling is performed further downstream, such as at point B or point A. When the combustion gases reach points B or A, not only is the combustion complete but CO burnout also should be complete, and the concentration of CO should be stable.

The invention can also be generalized to include determining the concentration of unburned hydrocarbons, volatile organic compounds (VOCs), and smoke. As in the case of other exhaust components, the sampling of the unburned hydrocarbons, VOCs, and smoke should take place at a position sufficiently downstream such that the concentration of the substance of interest has stabilized.

The method of the present invention has the advantage that it can be practiced with a single probe inserted into the combustor, as shown. The method of the invention eliminates the need for complex sampling rakes, and does not require determination of mass flow rate profiles in the gas stream. It also eliminates the need for expensive cooling devices to cool the sampling rakes. Also, in the present invention, the probe can be located at more convenient locations, such as at ground level, as compared with probes used in the prior art.

The method of the present invention could be used to determine the emission level of any one of the combustors of an engine having multiple combustors. The emission level can be calculated from a simple measurement of concentration as described above, and from knowledge of the fuel flow rate and fuel composition. Using the same method, one can also determine the emission level of an entire engine, if all of the combustors have the same structure and their fuel flow rates are the same.

TABLE 1

| | | | NOx | | |
|---|---|---|---|---|---|
| Power MW | Combustor Inlet NOx-ppmvd | Combustor Number 8 NOx-ppmvd | Engine Exhaust Measured NOx-ppmvd | Engine Exhaust Calc. from #8 Data NOx-ppmvd | Engine Exhaust $NOx_{meas}/NOx_{calc}$ |
| 10 | 24.5 | 53.7 | 36 | 37.3 | 0.97 |
| 25 | 31.4 | 83 | 55.5 | 52.5 | 1.06 |
| 56 | 39 | 126 | 74.2 | 72.1 | 1.03 |
| 75 | 41.5 | 135 | 80 | 77.5 | 1.03 |
| 110 | 43.5 | 146.5 | 85 | 81.9 | 1.04 |

The method of the present invention can therefore be used to test an experimental combustor, and to compare it with a neighboring combustor of standard design. The present invention avoids the need to test the overall emissions of the engine, since such emissions can be determined by measurements taken in the modified combustor.

Figure 5:
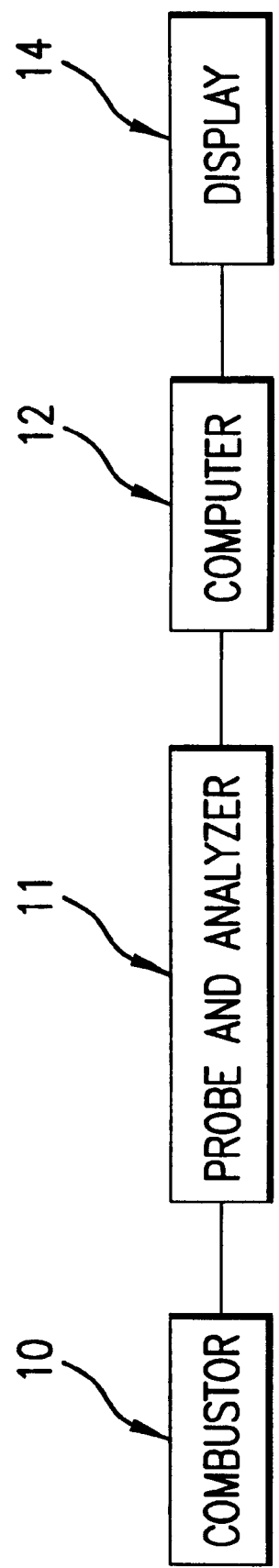
FIG. 5 provides a block diagram showing an apparatus which employs the method of the present invention.

In the above description, the invention has been characterized as a method used in the development of new structures for combustors. The invention can also be incorporated into apparatus which forms a permanent part of an engine. FIG. 5 provides a block diagram which illustrates one such apparatus. Combustor 10 of FIG. 5 may be similar in structure to that of FIG. 4, or its equivalent. The combustor is connected, by a sampling probe, to analytical device or analyzer 11, which measures the concentration(s) of gas components of interest, and converts the output to a voltage which can be used by a computer or equivalent device. The block diagram of FIG. 5 is not limited according to the position of the probe; FIG. 5 is intended to include all possible positions. The output signal from analytical device 11 is connected to computer 12, which may be any automated device which is programmed to receive numerical inputs from device 11, and to perform the calculations described above. Thus, the computer could be programmed to calculate, on a continuous basis, the exhaust concentration of NOx or other gaseous component.

The computer is connected to display module 14, which could be a video monitor or other display or indicator, or even a simple alarm device. When the computer determines that the concentration of NOx (or other component of interest) is greater than a predetermined level, or that the concentration falls outside of a predetermined range, the computer can transmit an appropriate message which can be viewed on the display. Alternatively, the message can take the form of an audible alarm.

The computer could also be programmed to reduce load on or shut down the engine in the event that the predetermined value is reached or exceeded. In this way, the invention can be used as a diagnostic tool which is a permanent part of the engine. In the most general case, one could include a probe, and its associated analyzer, in each combustor of the engine. Each such analyzer could be connected to its own computer or microprocessor, or to a different port on a single computer or microprocessor. The system could then provide an alert whenever the calculated NOx concentration implied by any one combustor exceeds the predetermined limit or falls outside a predetermined range.

The diagnostic tool described above could be used to indicate deterioration of a combustor caused by damage or wear and tear. An increase in emissions concentration could be the result of such deterioration. Thus, the signal generated by the apparatus described above could indicate that one of the combustors in the engine needs maintenance or replacement.

The diagnostic tool described above can also provide information about non-uniformity among the various combustors of an engine. The computer can continuously determine emissions for each combustor, based on the inputs received from each sampling probe and analytical device, and can be programmed to provide a warning if the emissions calculated for any one combustor falls too far outside the average level for the ensemble.

The invention is not limited to an engine having an annular array of individual combustors. Other arrangements are possible. The method of the present invention should also work for combustion systems which use one or two externally mounted chambers, or silos, which may contain multiple burner nozzles, each silo taking the place of more than one combustor. The method should also work where the combustion chamber is a full annulus, wherein the plurality of combustors are effectively merged, and multiple nozzles are disposed in an annular chamber. In these cases, multiple individual burners or modules are arranged at the head end of the combustors. The probe of the present invention could be located downstream of an individual burner of interest. The results would be the same.

The invention can be further modified in various ways, as will be apparent to those skilled in the art. Such modifications should be considered within the spirit and scope of the following claims.

What is claimed is:

1. A method of determining concentration of an exhaust component in an engine having a plurality of combustors, the method comprising the steps of:
   a) selecting one of said plurality of combustors for modification, and modifying said selected combustor,
   b) operating said selected combustor, while measuring concentration (A) of said exhaust component in said selected combustor, and while measuring concentration (B) of carbon dioxide ($CO_2$) in said selected combustor,
   c) computing concentration (C) of carbon dioxide in an exhaust of the engine, the computing step being based on engine air flow, fuel flow, and fuel hydrogen/carbon ratio, and
   d) calculating concentration (D) of said exhaust component according to the equation $$D=(A/B) \times C.$$

2. The method of claim 1, wherein said exhaust component is selected to be NOx.

3. The method of claim 1, wherein said exhaust component is selected to be CO.

4. The method of claim 1, wherein said exhaust component is selected from the group consisting of smoke, unburned hydrocarbons, and volatile organic compounds.

5. The method of claim 1, wherein step (b) includes selecting a point in the selected combustor at which production of said exhaust component is essentially complete, and sampling gas flow in the selected combustor at said point.

6. The method of claim 5, wherein said point is also selected to be a location at which combustion gases in the selected combustor are well mixed.

7. The method of claim 5, wherein the selected combustor includes a diluent air inlet, and wherein said selected point is chosen to be upstream of said diluent air inlet.

8. The method of claim 5, wherein the selected combustor includes a diluent air inlet, and wherein said selected point is chosen to be downstream of said diluent air inlet.

9. The method of claim 1, wherein the step of measuring concentration of said exhaust component is performed by sampling said exhaust component with a single probe.

10. A method of determining concentration of an exhaust component in an engine having a plurality of combustors, the method comprising the steps of:
    a) selecting a combustor from said plurality of combustors,
    b) operating the selected combustor, while measuring concentration (A) of said exhaust component in the selected combustor, and while measuring concentration (B) of carbon dioxide ($CO_2$) in the selected combustor,
    c) computing concentration (C) of carbon dioxide in an exhaust of the engine, the computing step being based on engine air flow, fuel flow, and fuel hydrogen/carbon ratio, and d) calculating concentration (D) of said exhaust component according to the equation $$D=(A/B)\times C.$$

11. The method of claim 10, wherein said exhaust component is selected to be NOx.

12. The method of claim 10, wherein said exhaust component is selected to be CO.

13. The method of claim 10, wherein said exhaust component is selected from the group consisting of smoke, unburned hydrocarbons, and volatile organic compounds.

14. The method of claim 10, wherein step (b) includes selecting a point in the selected combustor at which production of said exhaust component is essentially complete, and sampling gas flow in the selected combustor at said point.

15. The method of claim 14, wherein said point is also selected to be a location at which combustion gases in the selected combustor are well mixed.

16. The method of claim 14, wherein the selected combustor includes a diluent air inlet, and wherein said selected point is chosen to be upstream of said diluent air inlet.

17. The method of claim 14, wherein the selected combustor includes a diluent air inlet, and wherein said selected point is chosen to be downstream of said diluent air inlet.

18. The method of claim 10, wherein the step of measuring concentration of said exhaust component is performed by sampling said exhaust component with a single probe.

19. A method of monitoring performance of a gas turbine engine, the engine having a plurality of combustors, the method comprising the steps of:
a) providing a single probe for each of said combustors, said probe comprising means for sampling concentration (A) of an exhaust component of interest and for sampling concentration (B) of carbon dioxide ($CO_2$),
b) computing a concentration (C) of carbon dioxide in an exhaust of the engine, the computing step being based on engine air flow, fuel flow, and fuel hydrogen/carbon ratio, and
c) calculating, for each combustor, a concentration (D) of said exhaust component according to the equation $$D=(A/B)\times C.$$

20. The method of claim 19, wherein said exhaust component is selected to be NOx.

21. The method of claim 19, wherein said exhaust component is selected to be CO.

22. The method of claim 19, wherein said exhaust component is selected from the group consisting of smoke, unburned hydrocarbons, and volatile organic compounds.

23. The method of claim 19, wherein step (a) includes selecting a point in each combustor at which production of said exhaust component is essentially complete.

24. The method of claim 23, wherein said point is also selected to be a location at which combustion gases in the selected combustor are well mixed.

25. The method of claim 23, wherein the combustor includes a diluent air inlet, and wherein said selected point is chosen to be upstream of said diluent air inlet.

26. The method of claim 23, wherein the combustor includes a diluent air inlet, and wherein said selected point is chosen to be downstream of said diluent air inlet.

27. The method of claim 19, further comprising the step of activating an indicating means when any of concentrations D fall outside a predetermined range.

28. In a combustor, the combustor defining a housing, the improvement comprising:
a) single probe means inserted into the housing to a distance sufficient to sample combustion gas flowing within the housing, and
b) computer means, connected to receive data from said single probe means, the computer means being programmed to compute a concentration (D) of an exhaust component according to the equation $$D=(A/B)\times C,$$

where A is a concentration of said exhaust component as sampled by said single probe means, B is a concentration of carbon dioxide ($CO_2$) as sampled by said single probe means, and C is a computed concentration of carbon dioxide, in an exhaust of the combustor, based on air flow, fuel flow, and fuel hydrogen/carbon ratio.

29. The improvement of claim 28, wherein said single probe means is inserted into the housing at a point at which reactions involving said exhaust component have been substantially completed.

30. The improvement of claim 29, wherein said point is also selected to be a location at which combustion gases in the combustor are well mixed.

31. The improvement of claim 28, wherein the computer means is connected to an indicating means.

32. The improvement of claim 31, wherein the computer means is programmed to activate the indicating means when the concentration (D) falls outside a predetermined range.

33. A combustor for a gas turbine, the combustor defining a housing having fuel and air inlets, the housing defining a path for flow of combustion gases, the combustor having a single probe extending into an interior region of the housing, the probe comprising means for sampling concentrations of gases flowing along said path, the probe being connected to a computer means, the computer means being programmed to compute a concentration (D) of an exhaust component according to the equation $$D=(A/B)\times C,$$

where A is a concentration of said exhaust component as sampled by said single probe, B is a concentration of carbon dioxide ($CO_2$) as sampled by said single probe, and C is a computed concentration of carbon dioxide, in an exhaust of the combustor, based on air flow, fuel flow, and fuel hydrogen/carbon ratio.

34. The combustor of claim 33, wherein the probe is connected to the computer through an analyzer.

35. The combustor of claim 33, wherein the single probe extends into the housing at a point at which reactions involving said exhaust component have been substantially completed.

36. The combustor of claim 35, wherein said point is selected to be a location at which combustion gases in the combustor are well mixed.

37. The combustor of claim 33, wherein the probe comprises a heavy-walled tube which protrudes into the housing.

* * * * *